United States Patent [19]
Stroot

[11] 3,979,778
[45] Sept. 14, 1976

[54] SHOULDER PROSTHESIS
[76] Inventor: Jerome H. Stroot, 2645 Ocean Ave., San Francisco, Calif. 94132
[22] Filed: Jan. 14, 1976
[21] Appl. No.: 648,876

[52] U.S. Cl. .................................. 3/1.91; 128/92 C
[51] Int. Cl.² .......................................... A61F 1/24
[58] Field of Search ........................... 3/1.9–1.913, 3/1; 128/92 C, 92 CA

[56] References Cited
UNITED STATES PATENTS

| 3,228,393 | 1/1966 | Michele | 128/92 CA |
| 3,641,590 | 2/1972 | Michele | 3/1.912 |
| 3,694,820 | 10/1972 | Scales et al. | 3/1.91 |
| 3,803,641 | 4/1974 | Golyakhovsky | 3/1.91 |
| 3,839,742 | 10/1974 | Link | 3/1.91 |

OTHER PUBLICATIONS

"Richards, H–J–B Shoulder Prosthesis" (Advertisement), Richards Manufacturing Co., Memphis, Tenn., The Journal of Bone & Joint Surgery, vol. 46–A, No. 2, Mar. 1964, Advertisement p. 17.

Primary Examiner—Ronald L. Frinks
Attorney, Agent, or Firm—Robert G. Slick

[57] ABSTRACT

A total shoulder prosthesis is provided giving greater freedom of movement than structures heretofor available. The invention also includes a novel humeral component which can be used for a partial prosthesis.

4 Claims, 9 Drawing Figures

SHOULDER PROSTHESIS

SUMMARY OF THE INVENTION

Prostheses are available for the total replacement of the shoulder joint which consist of two components, namely, a humeral component and a glenoid component which fit together forming a ball and socket joint. The results are generally good except that the freedom of movement is very substantially restricted. Thus, the use of a ball and socket joint is useful primarily for older patients and is not suitable for younger people who wish to lead a very active life.

In accordance with the present invention, a shoulder prosthesis is provided which consists of a humeral and a glenoid component each of which has spherical articular surface but the radius of curvature of the glenoid component is substantially greater than that of the humeral component, providing what might be called a wandering fulcrum. The prosthetic shoulder of the present invention has a freedom of movement approximating that of a natural shoulder.

The invention also includes a novel humeral component having V-shaped notches in the lower portion of the articular surface which provides for the preservation and reattachment of the subscapularis and infrascapularis-teres minor tendons.

Accordingly, the present invention provides a shoulder prosthesis allowing greater freedom of movement than any prosthesis hertofor known.

DESCRIPTION OF THE PREFERRED EMBODIMENTS

Figure 1:
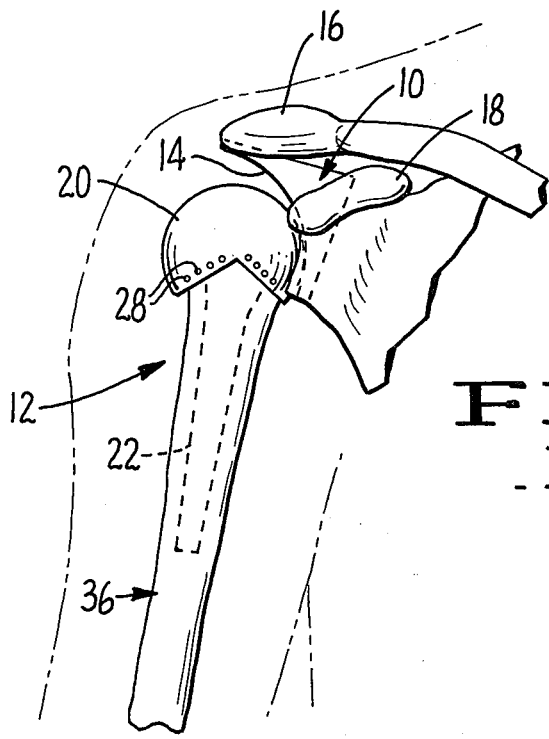
FIG. 1 is an anterior view showing the prosthesis of the present invention in place.

Referring now to the drawings by reference characters, the prosthesis of the present invention comprises two parts, namely a glenoidal component generally designated 10 and a humeral component designated 12.

The glenoid component 10 has a concave hemispherical articular surface 14. The glenoidal component replaces most or all of the glenoid cavity, i.e. the articular surface of the glenoid, and has a back surface which extends to the spine 16 of the acromion behind and the coracoid process 18 in front. In this manner there is created a coraco-acromial arch. The glenoidal component 10 is fixed to bone with glue or cement at points of contact with the glenoid, acromion and coracoid process in a manner well known to those skilled in the art.

The humeral component has a spherical head 20 and a shaft or stem 22 for connecting it to the medullary canal of the humerus. The head 20 has a lower edge with a front V-shaped notch 24 and a rear notch 26. A series of holes 28 surrounds the V-shaped notches, the purpose of which will be brought out later.

According to the present invention the radius of curvature of the glenoid component is much greater than that of the humeral component and the ratio of the two radii can vary from one and one-half to three times.

Figure 2:
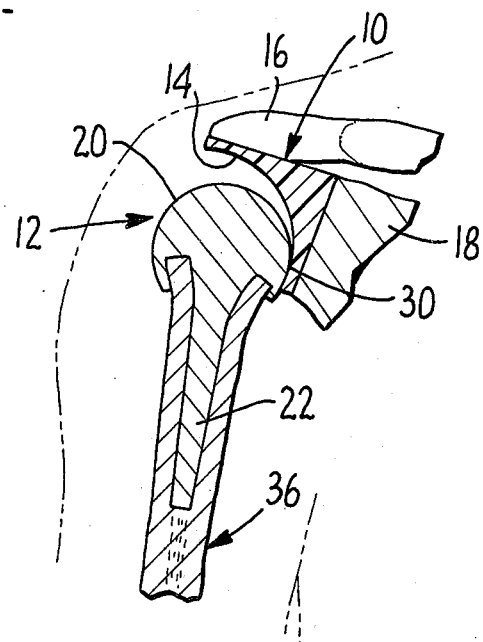
FIG. 2 shows a section through the prosthesis of the present invention showing the position of the parts when the arm is in the down position.
Figure 3:
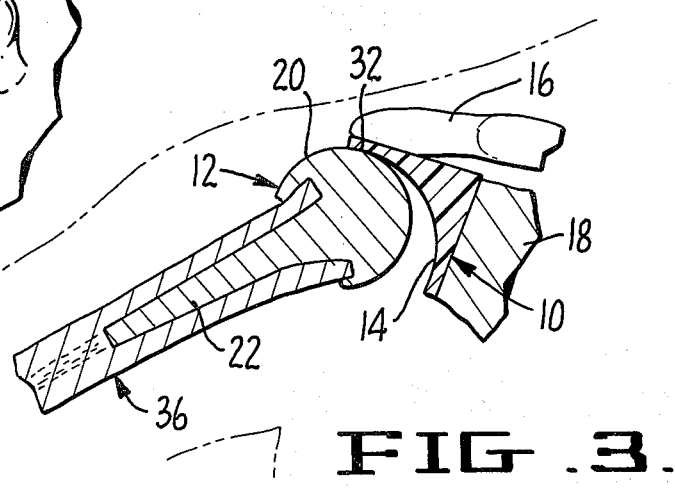
FIG. 3 is a view similar to FIG. 2 showing the position of the parts when the arm is in an upper position.
Figure 5:
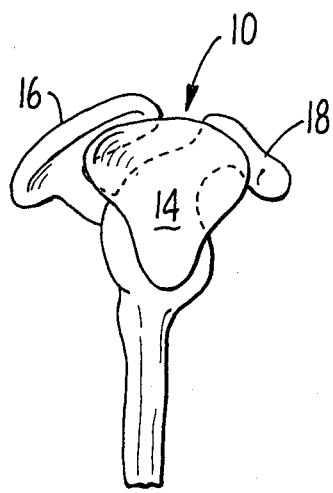
FIG. 5 is a side view of the prosthesis of the present invention.
Figure 6:
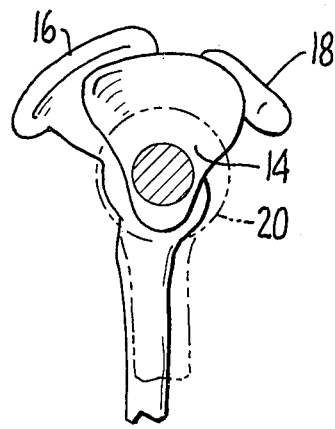
FIG. 6 is a view, similar to FIG. 5, showing certain of the parts in section.
Figure 7:
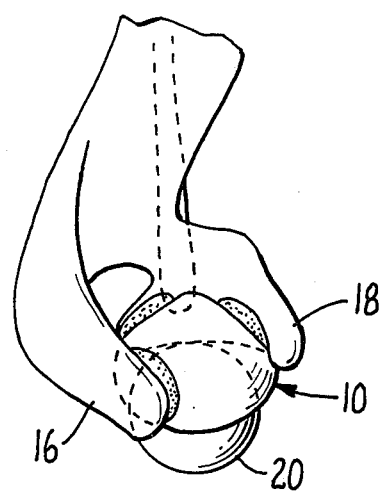
FIG. 7 is a top perspective view of the prosthesis of the present invention.

The greater freedom of movement provided by this relationship is most clearly shown in FIGS. 2 and 3. In FIG. 2 a right shoulder is shown with the arm in a down position with the area of contact shown at 30. FIG. 3 shows the arm in a raised position and now the point of contact has moved to 32. It can thus be seen that greater freedom of movement is provided than with the usual ball and socket joint. Although this has only been illustrated in conjunction with up and down movement, it will be apparent that the same freedom of motion is achieved with front to rear movement.

Figure 4:
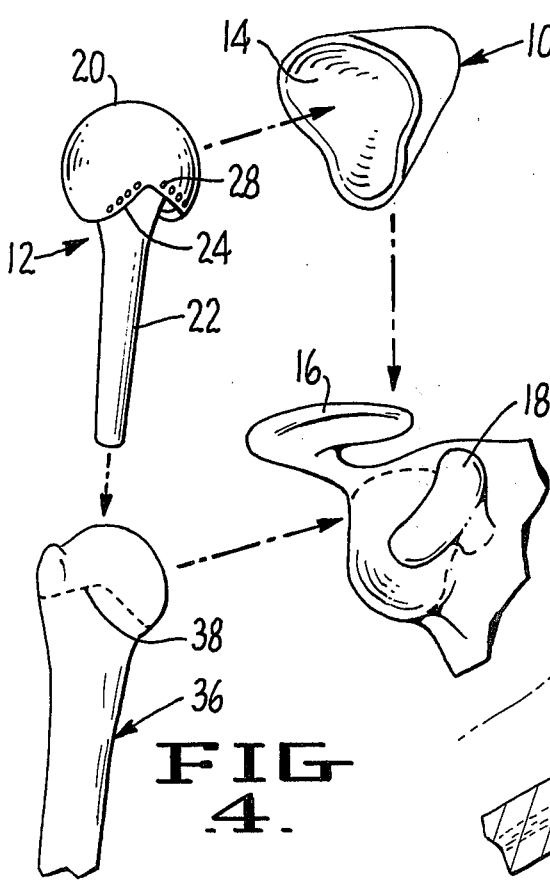
FIG. 4 is an exploded perspective view showing the method of preparation of the patient and the attachment of the two prosthesis components.

The method of utilizing the prosthesis of the present invention is shown in FIG. 4. The upper half of the glenoid is removed to the base of the coracoid and the glenoid is excavated except for the outer rim. The glenoid component 10 is then fastened between the spine of the acromion 16 and the coracoid process 18. The glenoid component is fixed to the bone with glue or cement as is well known to those skilled in the art.

The humerus 36 is prepared for the prosthesis by decapitating it substantially on the line 38 and the entire upper end of the humerus is removed and not just the articular portion. Shaft 22 is then placed in the medullary canal and fastened to the cancellous bone with glue or cement.

Figure 8:
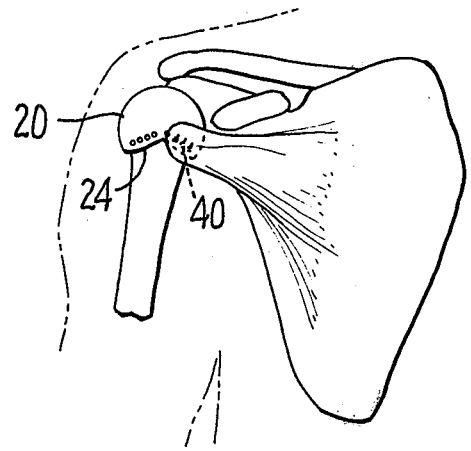
FIG. 8 is an anterior view showing the method of attachment of the front tendons to the humeral component.
Figure 9:
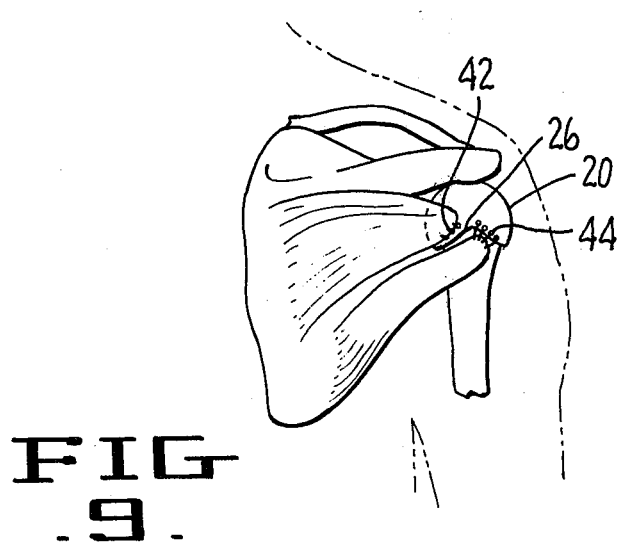
FIG. 9 is a posterior view of the humeral component showing the attachment of the rear tendons.

The holes in the V-shaped notches at the bottom of the spherical portion 20 of the humeral component are used for the passage of sutures and the fixation of tendons to bone. Thus, as is shown in FIG. 8, the subscapularis tendons 40 are attached to the front of the ball. The infraspinatus and teres minor tendons 42 and 44, respectively, are both fastened at the rear of the ball as is shown in FIG. 9.

Although the prosthesis of the present invention was primarily designed as a total shoulder prosthesis, in those cases where the glenoid is intact, the humeral component can be used in a partial prosthesis. In such a case, the radius of curvature of the humeral component bears the same ratio to the natural glenoid as it would to the prosthetic glenoid described above.

It is believed apparent in the foregoing that I have provided shoulder prosthesis which allows much greater freedom of action than the shoulder prosthesis heretofore known. I have also provided humeral components of generally improved design which allows the preservation and reattachment of the subscapularis and infraspinatus and teres minor tendons, and allows a greater range of motion by replacing the tuberosites (which impede abduction) with a spherical ball replacing the entire upper end of the humerus.

I claim:

1. A total shoulder prosthesis comprising in combination:

a. a humeral component having a spherical end and means for fastening said humeral component to a decapitated humerus, b. a glenoid component including a socket adapted to replace a normal glenoid cavity and means for attaching said glenoid component between the spine of the acromion and the coracoid process wherein;

c. the radius of curvature of said socket is greater than the radius of curvature of said spherical end whereby the fulcrum point of the prosthesis moves as the humeral component moves with respect to the glenoid component.

2. The prosthesis of claim 1 wherein said humeral component has a shaft extending opposite said hemispherical end with a V-shaped notch on the front and back surfaces of the lower terminal edge of the hemispherical end and having a plurality of holes along the edges of the V-shaped notches.

3. The prosthesis of claim 1 wherein the ratio of the radius of curvature of the socket to the ball is from 1.5 to 3.

4. A humeral component for a shoulder prosthesis comprising in combination:

a. a first end having a spheroidal shape, b. a second end including a shaft for attaching said component to a decapitated humerus, c. said first end terminating in a lower edge having V-shaped notches at the front and back thereof, and a plurality of holes surrounding said notches.

* * * * *